United States Patent [19]

Chandraratna

[11] Patent Number: 5,015,658

[45] Date of Patent: * May 14, 1991

[54] THIOCHROMAN ESTERS OF PHENOLS AND TEREPHTHALLATES HAVING RETINOID-LIKE ACTIVITY

[75] Inventor: Roshantha A. S. Chandraratna, El Toro, Calif.

[73] Assignee: Allergan, Inc., Irvine, Calif.

[*] Notice: The portion of the term of this patent subsequent to Jan. 23, 2007 has been disclaimed.

[21] Appl. No.: 366,831

[22] Filed: Jun. 15, 1989

Related U.S. Application Data

[63] Continuation-in-part of Ser. No. 212,855, Jun. 29, 1988, Pat. No. 4,895,868.

[51] Int. Cl.⁵ .................. A61K 31/38; C07D 335/06
[52] U.S. Cl. .................................. 514/432; 514/863; 549/23
[58] Field of Search ................ 549/23; 514/432, 863

[56] References Cited

U.S. PATENT DOCUMENTS 4,788,213  11/1988  Klaus et al. .................. 549/23
4,895,868   1/1990  Chandraratna ................ 549/23

Primary Examiner—Mary C. Lee
Assistant Examiner—Jacqueline Haley
Attorney, Agent, or Firm—Gabor L. Szekeres; Martin A. Voet; Robert J. Baran

[57] ABSTRACT

Compounds of formula I

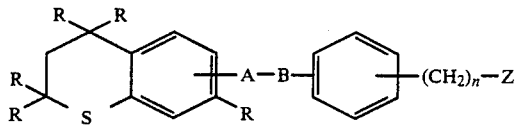

in which:

the R groups are independently hydrogen or lower alkyl; one of A and B is O or S and the other is —C(O)—, A being attached to the thiochroman ring at the 6 or 7-position;

n is 0–5; and

Z is H, an acid or acid derivative, an alcohol or alcohol derivative, acetal or acetal derivative or ketone or ketone derivative, or a pharmaceutically acceptable salt, have retinoid-like activity.

16 Claims, No Drawings

THIOCHROMAN ESTERS OF PHENOLS AND TEREPHTHALLATES HAVING RETINOID-LIKE ACTIVITY

CROSS-REFERENCE TO RELATED APPLICATION

The present application is a continuation-in-part of application Ser. No. 212,855, filed on Jun. 29, 1988, now issued as U.S. Pat. No. 4,895,868, assigned to the same assignee as the present application.

This invention relates to novel compounds having retinoid-like activity. These compounds are esters containing a thiochroman group.

1. Related Art

The compound 4-(5,5,8,8-tetramethyl-5,6,7,8-tetrahydro-2-naphthoylamino)benzoic acid is disclosed in Sporn et al., *J. Amer. Acad. Derm.* 15:756–764 (1986). See also the several compounds disclosed in Shudo et al., *Chem. Pharm. Bull.* 33:404–407 (1985).

2. The Invention

This invention relates to the following compounds:

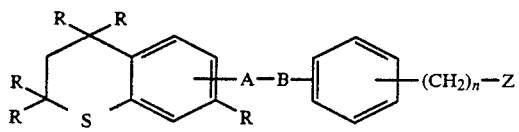

in which:
the R groups are independently hydrogen or lower alkyl; one of A and B is O or S and the other is —C(O)—, A being attached to the thiochroman ring at the 6 or 7-position;
n is 0–5; and
Z is H, or Z is —COD where D is —OH or a pharmaceutically acceptable salt, or D is —OR$_1$ where R$_1$ is an ester-forming group, or D is —N(R$_4$)$_2$ where R$_4$ is hydrogen or an aliphatic or substituted aliphatic group, or Z is —OE where E is hydrogen or an ether-forming group or an acyl ester forming group, or Z is —CHO or an acetal derivative thereof, or Z is —COR$_3$ where R$_3$ is —(CH$_2$)$_m$CH$_3$ where m is 0–4 and the sum of n and m does not exceed 4 or a ketal derivative thereof.

This invention also relates to a pharmaceutical composition comprising a compound of formula I in admixture with a pharmaceutically acceptable excipient.

In addition, this invention relates to the use of the compounds of formula I for treating dermatoses, such as acne, Darier's disease, psoriasis, icthyosis, eczema, atopic dermatitis and epithelial cancers. These compounds are also useful in the treatment of arthritic diseases and other immunological disorders (e.g., lupus erythematosus), in promoting wound healing, in treating the dry eye syndrome, and in preventing and/or reversing the effects of sun induced skin aging and damage.

In another aspect, this invention relates to the process for making a compound of formula I which process comprises reacting a compound where the A' or B' of formula II or III is an acid or acid derivative which can form an ester with the corresponding formula II or III where A' or B' is —OH or —SH, preferably in the presence of an ester-forming catalyst.

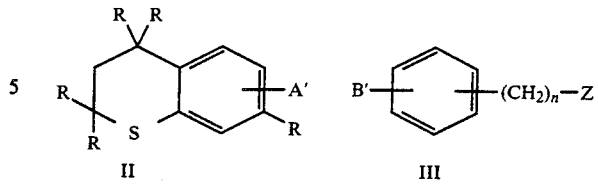

Here, R, n and Z are defined above, with the proviso that if Z is an acid or alcohol function, it is preferred that it be protected. Where Z is an aldehyde or ketone, such functional groups need not be protected in order to effect this reaction.

Secondly deprotecting a protected compound obtained by the foregoing ester-forming reaction using deprotecting means gives the corresponding acid, alcohol, aldehyde or ketone, of Formula I, as appropriate if such protected compound has been prepared and is to be converted to the parent functional group. Acids of formula I may be converted to their salts by treating them with the appropriate base under mild conditions. An acid of formula I can also be converted to an ester. Alcohols of formula I may be made from the corresponding aldehydes by reducing means.

To synthesize compounds where n is 1 or greater, and the corresponding formula III form is not commercially available, the acid form of formula III (Z is COOH) can be homologated to insert the desired number of methylene groups. This homologation product, the acid, can then be reduced to give the corresponding aldehyde or alcohol. Aldehydes can be converted to their ketone analogues. Such compounds can then be coupled with the corresponding formula II compound, the functional group represented by Z being protected as necessary.

GENERAL EMBODIMENTS

Definitions

The nomenclature employed herein is exemplified by the following molecular structure of a thiochroman moiety.

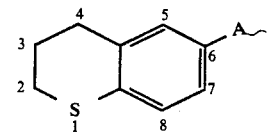

The term "ester" as used here refers to and covers any compound falling within the definition of that term as classically used in organic chemistry. It includes organic and inorganic esters. Where Z is —COOH, this term covers the products derived from treatment of this function with alcohols or thiols. Where the ester is derived from compounds where Z is —OH, this term covers compounds derived from organic acids capable of forming esters including phosphorous-based and sulfur-based acids.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkylphenyl esters.

The term "lower alkyl" as used herein means an alkyl radical of 1 to 6 carbon atoms.

Ether derivatives may be prepared for any of the compounds where Z is —OH. Preferred ethers are those derived from an aliphatic radical of 1 to 20 carbon atoms, phenyl or aliphatic-phenyl radical where the aliphatic group has up to 20 carbon atoms. In this last instance, the phenyl group can be on the omega position of the aliphatic chain or at another position on that chain. Also cyclic radicals of 5–7 carbons and aliphatic-cyclic radicals of up to 20 carbons are preferred.

Amides has the meaning classically accorded that term in organic chemistry. In this instance it particularly includes the unsubstituted amides and all aliphatic and aromatic mono- and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and di-substituted amides derived from the substituted and unsubstituted phenyl or lower alkylphenyl amines. Unsubstituted amides are also preferred.

Acetals and ketals includes radicals of the formula —CK where K is (—OR)$_2$. Here, R is lower alkyl. Also, K may be —OR$_3$O— where R$_3$ is lower alkyl of 2–5 carbon atoms, straight chain or branched.

In preferred compounds of formula I, A is attached to the thiochroman ring at the 6- or 7-position. Also preferred are those of formula I where the (CH$_2$)$_n$-Z substituent is para to the ester function on the phenyl ring; n is 0, 1 or 2; and Z is —COOH, an alkali metal salt or organic amine salt, or a lower alkyl ester, or —OH and the lower alkyl esters and ethers thereof. Particularly preferred compounds are:

ethyl 4-(2,2,4,4,7-pentamethyl-6-thiochromanoyloxy)-benzoate,
4-(2,2,4,4,7-pentamethyl-6-thiochromanoyloxy)benzoic acid,
4-(4,4,7-trimethyl-6-thiochromanoyloxy)benzoic acid,
ethyl 4-(2,2,4,4-tetramethyl-7-thiochromanoyloxy)benzoate,
ethyl 4-(4,4,7-trimethyl-6-thiochromanoyloxy)benzoate;
ethyl 4-(4,4-dimethyl-6-thiochromanoyloxy)benzoate;
4-(4,4-dimethyl-6-thiochromanoyloxy)benzoic acid;
4-(4,4-dimethyl-7-thiochromanoyloxy)benzoic acid;
ethyl 4-(4,4-dimethyl-7-thiochromanoyloxy)benzoate;
ethyl 4-(2,2,4,4-tetramethyl-6-thiochromanoyloxy)benzoate; and
4-(2,2,4,4-tetramethyl-6-thiochromanoyloxy)benzoic acid.

A pharmaceutically acceptable salt may be prepared for any compounds in this invention having a functionality capable of forming such salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts from mono-, di- and trialkly amines or ethanol amines. Salts may also be formed with caffeine, tromethamine and similar molecules.

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, Remington's Pharmaceutical Science, Edition 17, Mack Publishing Company, Easton, Pa. For topical application, these compounds could also be administered as a powder or spray, particularly in aerosol form.

If the drug is to be administered systemically, it may be confected as a powder, pill, tablet or the like, or as a syrup or elixir suitable for oral administration. For intravenous or intraperitoneal administration, the compound will be prepared as a solution or suspension capable of being administered by injection. In certain cases, it may be useful to formulate these compounds in suppository form or as an extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in a prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.1 and 1.0 milligrams per milliliter of formulation will constitute a therapeutically effective concentration for topical application. If administered systemically, an amount between 0.01 and 5 mg per kg per day of body weight would be expected to effect a therapeutic result in the treatment of many diseases for which these compounds are useful.

The retinoic acid like activity of these compounds is confirmed through the classic measure of retinoic acid activity involving the effects of retinoic acid on ornithine decarboxylase. The original work on the correlation between retinoic acid and decrease in cell proliferation was done by Verma and Boutwell, *Cancer Research*, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all causes for ODC activity increase are unknown, it is known that 12-O-tetradecanoylphorbol-13-acetate (TPA) induces ODC activity. Retinoic acid inhibits this induction of ODC activity by TPA. The compounds of this invention also inhibit TPA induction of ODC as demonstrated by an assay essentially following the procedure set out in *Cancer Res.*: 1662–1670, 1975.

PREPARATION OF COMPOUNDS

It is anticipated that the compounds of this invention can be made by a number of different synthetic chemical pathways. To illustrate this invention, there is here laid out a series of steps which will provide the compounds of formula I when such synthesis is followed in tone and in spirit. The synthetic chemist will readily appreciate that the conditions set out here are specific embodiments which can be generalized to any and all of the compounds represented by formula I.

Compounds of formula I where A is —(O)C— and B is O are prepared as follows:

REACTIN SCHEME I

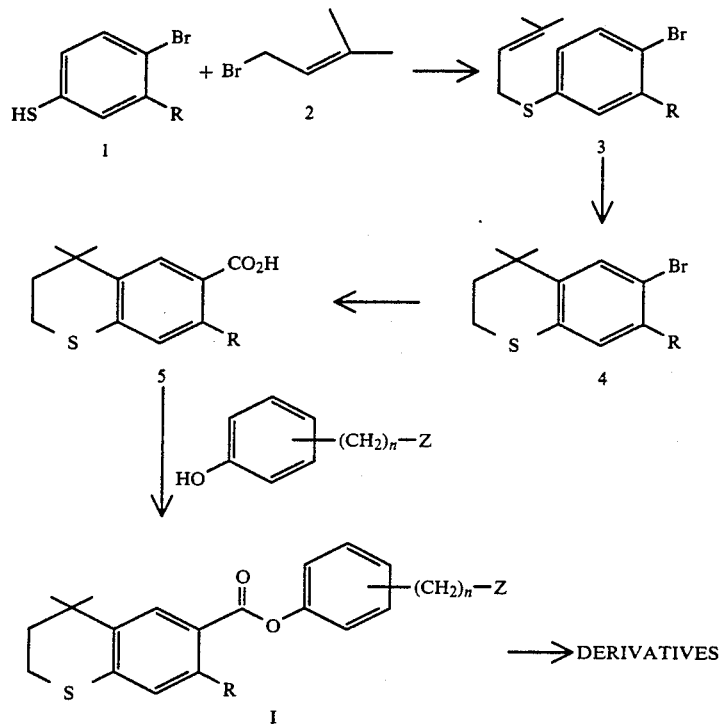

The definition of R and n are those given herein above. Z is H, an ester or amide of COOH, —OH or an ether or ester derivative, —CHO or an acetal derivative or —C(O)— or a ketal derivative.

Those compounds having the reverse connectivity, that is where A is O and B is —C(O)— can be made in the manner illustrated in Reaction Scheme II.

REACTON SCHEME II

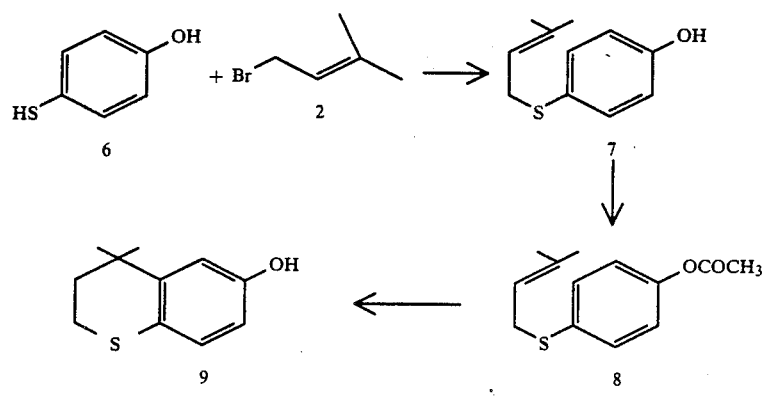

-continued

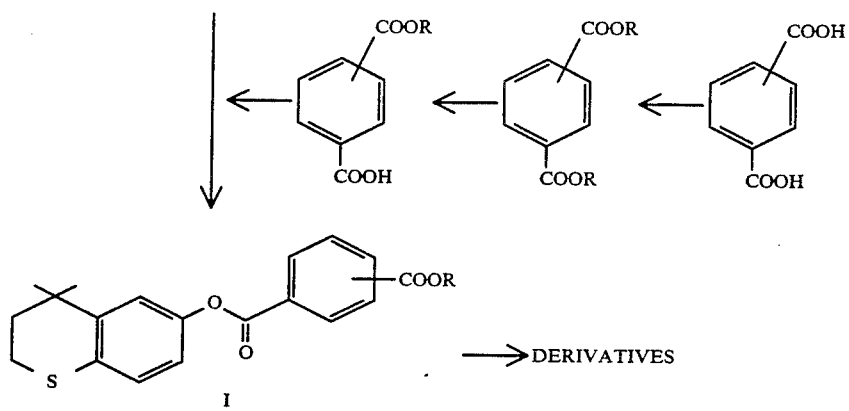

Compounds having two methyl groups at the 2 position of the thiochroman ring can be made by the sequence of steps outlined in Reaction Scheme III.

REACTION SCHEME III

REACTION SCHEME IV

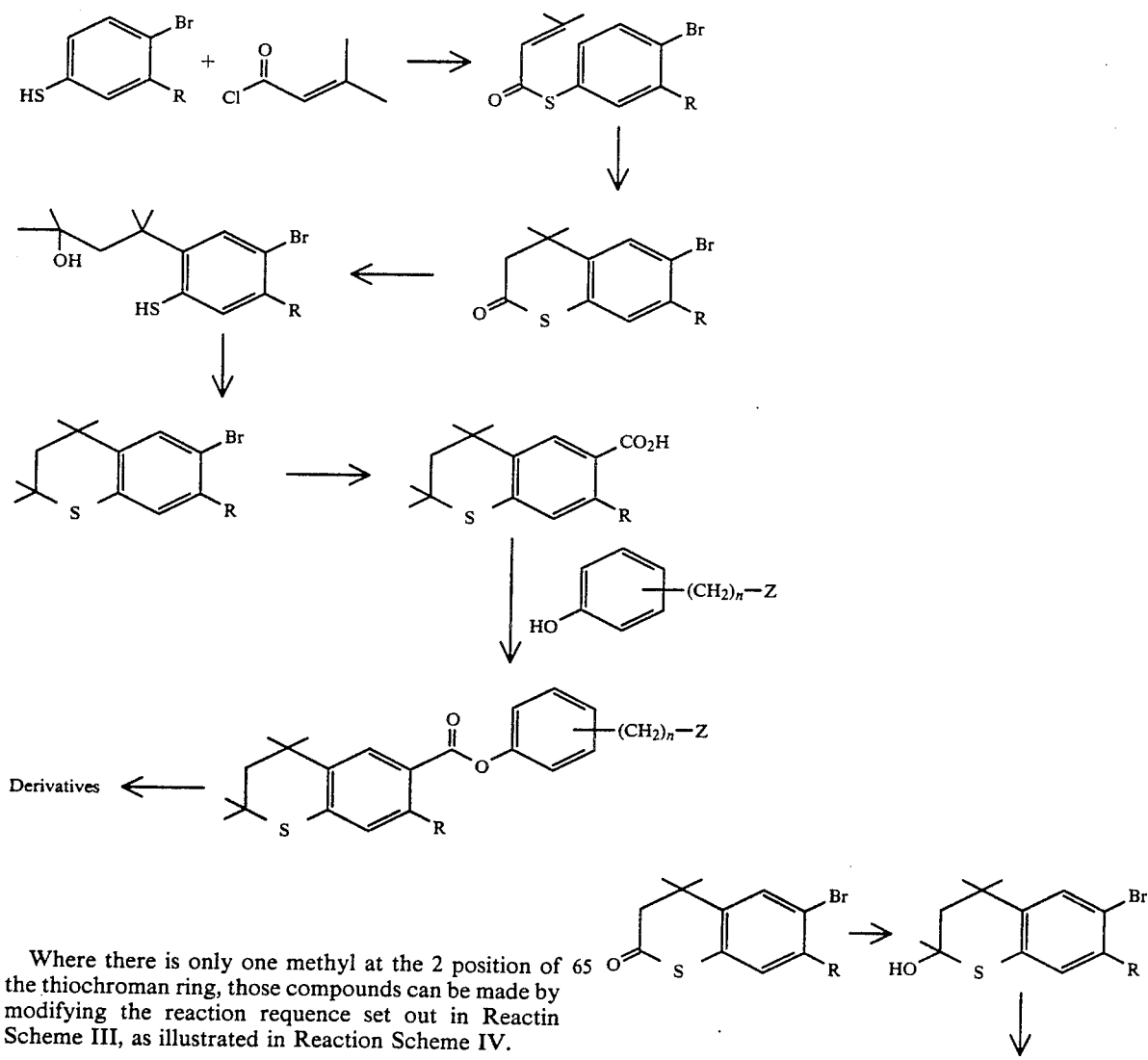

Where there is only one methyl at the 2 position of the thiochroman ring, those compounds can be made by modifying the reaction requence set out in Reactin Scheme III, as illustrated in Reaction Scheme IV.

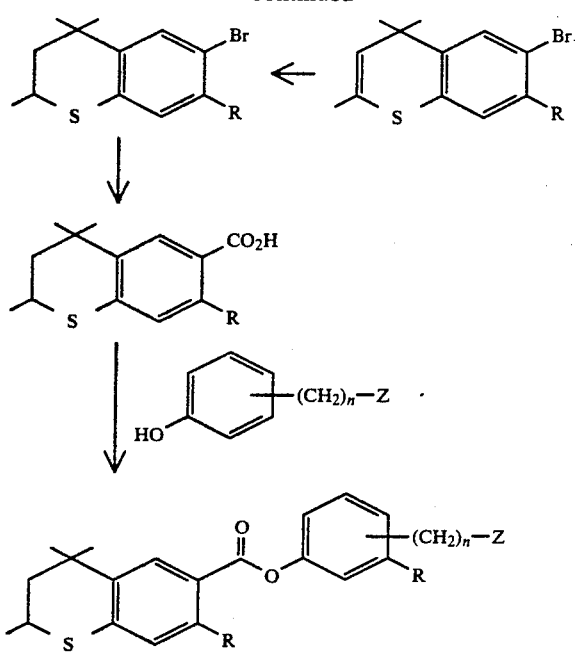

A general description of the chemistry for making compounds where the substituents at the 2-position of the thiochroman ring are hydrogen is recited as follows, or can be goten from a reading of the Examples.

The 4-bromothiophenol of formula 1 is first treated with approximately an equimolar amount of a strong base such as an alkali metal hydroxide, preferably sodium hydroxide, in a solvent such as acetone at reflux. Refluxing is carried out for between about 1 and 4 hours, preferably 2.5 hours, after which the solution is treated with an equimolar amount of formula 2, available from Aldrich Chemical Co. of St. Louis, MO, USA, dissolved in the selected solvent. Refluxing is continued for an extended time, up to about 2 days, after which the solution is stirred for another extended period, for example about 24 hours, at about room temperature. Product 3 is isolated by conventional means.

Ring closure is effected by adding the sulfide (compound 3) to a solution of phosphorous pentoxide and a strong acid such as methanesulfonic acid under an inert atmosphere to effect formation of the thiochroman of formula 4. The solution stirred under an inert gas such as argon or nitrogen for a short period, 10 minutes to 2 hours, at about ambient temperature. This mixture is then diluted with water, heated to a moderate temperature, about 30° to 50° C. and extracted with an appropriate solvent, ether for example. The product is further recovered and purified by conventional means.

The acid function of formula 5 is introduced by means of tert-butyl lithium or a similar base at reduced temperature under an inert atmosphere. The reaction is carried out in an ether-type of solvent such as a dialkyl ether or a cyclic ether, for example tetrahydrofuran, pyran or the like.

More specifically, a solution of the bromo compound is dissolved in an ether-type solvent. This solution is cooled, preferably to about between −70° and −50° C. An equimolar amount of an alkyl-lithium compound such as tert-butyl lithium in an appropriate solvent (an alkane or the like) is then added in portions at the reduced temperature and mixed for an appropriate time. Between about 30 minutes and 5 hours will effect the reaction. The reaction mixture is then treated with solid carbon dioxide and warmed to room temperature, the solution acidified and the product recovered by conventional means.

Coupling this acid, or its analoges, with the appropriate phenol or thiophenol gives compounds of formula I. Most means for esterification or thioesterification will provide the desired compounds of formula I. In these cases, esterification was effected by treating the appropriate acid and phenol with 1,3-dicyclohexylcarbodiimide and 4-dimethylaminopyridine.

Preparation of compounds with the reverse connectivity, that is where B is —C(O)—, is achieved by preparing the thiochroman compounds illustrated in Reaction Scheme II.

The 4-mercaptophenol (formula 6) is reacted with 1-bromo-3-methyl-2-butene under essentially the same conditions as recited above in the discussion of Scheme I chemistry. Protecting the free OH group of formula 7 by some means makes it possible to form the thiochroman by cyclization using the same means as described above in the discussion of the chemistries of Scheme I. Base hydrolysis of the OH protecting group during work-up results in a free OH group at position 6 on the resulting thiochroman of formula 9. This compound is then reacted with a terephthalate to give a compound with the desired core structure.

Terephthallic acids used in Scheme II are readily available from most chemical supply houses. Their esterification and selective hydrolysis to the mono-acid is illustrated for the para-substituted compound, but can be used for the general case of the terephthallates. The coupling reaction used to make the final product is the same or an obvious variation of the generalized reaction sequence and conditions given for Reaction Scheme I.

If the Z group is an alcohol, aldehyde or ketone, it can first be converted to an ether or ester, acetal or ketal respectively before being used in the foregoing coupling reaction. Alcohols may be protected as ethers or esters and aldehydes and ketones as acetals or ketals by known methods such as those described in McOmie, Plenum Publishing Press, 1973 and *Protecting Groups*, Ed. Greene, John Wiley & Sons, 1981. These same procedures can be used to make ethers, acetals and ketals at some other point in the synthetic process.

Alcohols are made by converting the corresponding acids of formula I to the acid chloride as described above, then reducing the acid chloride with sodium borohydride (March, Ibid, pg. 1124). Alternatively, the aldehydes of formula I can be reduced to the corresponding alcohols using sodium borohydride. Also, before effecting the coupling of formula II and formula III compounds, aldehydes of formula III can be reduced to the alcohol using sodium borohydride. Alkylating formula I or formula III alcohols with appropriate alkyl halides under Williamson reaction conditions (March, Ibid, pg. 357) gives the corresponding ethers.

Esterification may be accomplished by reacting the acid with the appropriate alcohol in the presence of coupling reagents such as 1,3-dicyclohexylcarbodiimide and 4-dimethylaminopyridine. The ester is recovered and purified by conventional means.

Amides may be formed by any appropriate amidation means known to the art. One way to prepare such compounds is to first make an acid chloride and then treat that compound with ammonium hydroxide or an appropriate amine. For example, the acid is treated with an alcoholic solution base such as ethanolic KOH (about one equivalent) and reacted at room temperature for about ½ hour. The solvent is removed and the residue taken up in an organic solvent such as ether, treated with a dialkyl formamide and then a 10-fold excess of oxalyl chloride. This is all effected at a reduced temperature between about −10° and +10° C. The last mentioned solution is then stirred at the reduced temperature for about 1–4 hours, preferably 2 hours. Solvent removal provides a residue of the acid chloride which is taken up in an inert inorganic solvent such as benzene, cooled to about 0° C. and treated with concentrated ammonium hydroxide. The resulting mixture is stirred at a reduced temperature for about 1–4 hours. The product is recovered by conventional means.

Aldehydes can be prepared from the corresponding primary alcohols using mild oxidizing agents such as exemplified by pyridinium dichromate in methylene chloride (Corey, E. J., Schmidt, G., Tet. Lett., 399, 1979).

Acetals can be prepared from the corresponding aldehyde by the method described in March, Ibid, p 810. There can then be reacted with formula II compounds to give acetals of formula IV.

The acids of formula I can be obtained from the esters of formula I. The terminal benzyl ester can be selectively cleaved using boron tribromide. For example, the ester in an inert solvent such as methylene chloride is cooled to low temperatures, about −10° C., under an inert gas. The cold solution is treated slowly with boron tribromide in methylene chloride and the mixture stirred at low temperatures for about 1–4 hours. The mixture is quenched and the product recovered by conventional means.

The salts are prepared by reacting the acid with an appropriate base under standard conditions.

Compounds of formula III where n is 1–5 may be prepared from compounds in which n is 0–4 and Z is COOH by homologation by successive treatment under Arndt-Eistert conditions and subsequent manipulation of the resulting acid as described above. These can be used to prepare compounds of formula I where n is 1–5 and Z is and alcohol, aldehyde or ketone or derivatives thereof.

The following examples are set out to illustrate the invention, not to limit its scope.

EXAMPLE 1

4-bromophenyl-3-methylbut-2-enylsulfide

A solution of 25 g (0.132 mmol) of 4-bromothiophenol and 5.56 g (0.139 mmol) of sodium hydroxide in 100 ml of acetone was heated at reflux for 0.5 hours. To the refluxing mixture was then added dropwise a solution of 19.7 g (0.132 mmol) of 1-bromo-3-methyl-2-butene in 30 ml of acetone. The reaction mixture was heated at reflux for a further 1.5 hours, cooled and the solvent then removed in-vacuo. The residue was taken up in water and extracted with ether. The ether extracts were combined and washed successively with dilute sodium hydroxide, water and saturated sodium chloride and then dried (calcium chloride). The solution was filtered and the filtrate concentrated in-vacuo. The residue was then fractionally distilled (124°–128° C.; 0.5 mm) to give the title compound as a colorless oil. PMR (CDCL$_3$): δ1.57 (3H, s), 1.69 (3H, s), 3.49 (2H, d, J~7.7 Hz), 5.25 (1H, m), 7.15 (2H, d, J. 8.6 Hz), 7.35 (2H, d, J~8.6 Hz).

EXAMPLE 2

4,4-dimethyl-6-bromothiochroman

To 10 ml of 1:10 (w/w) mixture of phosphorus pentoxide and methanesulfonic acid was added slowly with stirring 1.0 g (3.89 mmol) of 4-bromophenyl-3-methylbut-2-enylsulfide. The mixture was stirred at room temperature for 0.5 h and then poured into 150 ml water. The resultant mixture was heated up to 50° C., cooled to room temperature and extracted with two portions of ether. The ether extracts were combined and washed successively with water and saturated NaCl solution and then dried (MgSO$_4$). The solution was filtered and the solvent removed in-vacuo to give the title compound as pale yellow crystals. PMR (CDCl$_3$): δ1.30 (6H, s), 1.92 (2H, m), 3.01 (2H, m), 6.94 (1H, d, J~8.8 Hz), 7.13 (1H, dd, J~8.8 Hz, 2.2 Hz), 7.45 (1H, d, J~2.2 Hz).

EXAMPLE 3

4,4-dimethyl-6-carboxythiochroman

To a stirred solution of 5.14 g (0.02 mmol) of 4,4-dimethyl-6-bromothiochroman in 40 ml of dry ether at −78° C. was added dropwise 28.2 ml of 1.7M (0.048 mmol) tertbutyllithium in pentane. The mixture was stirred at −78° C. for 2.5 hours and then treated with an excess of solid carbon dioxide. The mixture was warmed to room temperature and treated with sufficient water to dissolve the solids. The aqueous layer was then separated, acidified with dilute sulfuric acid and extracted with three portions of ether. The ether extracts were combined and washed successively with water and saturated NaCl solution and then dried (MgSO$_4$). The solution was filtered and the solvent removed in-vacuo and the residue recrystallized from ethyl acetate and hexane to give the title compound as a white solid. PMR (CDCl$_3$): δ1.37 (6H, s), 1.97 (2H, m), 3.08 (2H, m), 7.17 (1H, d, J~8.0 Hz), 7.74 (1H dd, J~8.0, 1.9 Hz), 8.11 (1H, d, J~1.9 Hz).

EXAMPLE 4

Ethyl 4-(4,4-dimethyl-6-thiochromanoyloxy)benzoate

A solution of 280 mg (1.26 mmol) of 4,4-dimethyl-6-carboxythiochroman and 252 mg (2.52 mmol) of triethylamine in 15 ml of chloroform was stirred at room temperature for 0.5 hours and then treated with 481 mg (1.26 mmol) of bias(2-oxo-3-oxazolidinyl)phosphinic chloride. The reaction mixture was stirred for 0.5 h, treated with 209 mg (1.26 mmol) of ethyl 4-hydroxybenzoate and then stirred at room temperature for a further 12 hours. The reaction mixture was washed successively with dilute HCl and saturated sodium bicarbonate solutions. The organic layer was concentrated in-vacuo and the resultant crude product purified by flash chromatography (silica; 10% ethyl acetate in hexane) followed by reversed-phase high pressure liquid chromatography (Whatman Partisil M20 10/50 ODS-2; 10% water in acetonitrile) to give the title compound as a colorless oil. PMR (CDCl$_3$): δ1.38 (6H, s), 1.42 (3H, t, J~7.0 Hz), 1.98 (2H, m), 3.07 (2H, m), 4.39 (2H, q, J~7.0 Hz), 7.20 (1H, d, J~9.0 Hz), 7.28 (2H, d, J~8.1 Hz), 7.82 (1H, dd, J~9.0, 1.8 Hz), 8.12 (2H, d, J~8.1 Hz), 8.17 (1H, d, J~1.8 Hz).

EXAMPLE 5

Benzyl 4-(4,4-dimethyl-6-thiochromanoyloxy)benzoate

A solution of 786 mg (3.54 mmol) of 4,4-dimethyl-6-carboxythiochroman, 804 mg (3.53 mmol) of benzyl 4-hydroxybenzoate, 800 mg (3.88 mmol) of 1, 3-dicyclohexylcarbodiimide and 60 mg (0.49 mmol) of 4-dimethylaminopyridine in 50 ml of methylene chloride was stirred at room temperature for 2 hours. The reaction mixture was then filtered and the residue washed with 20 ml of methylene chloride. The filtrate was concentrated in-vacuo and the resultant crude product was purified by flash chromatography (silica, 20% ethyl acetate in hexanes) followed by recrystallization from a mixture of hexanes and ethyl acetate to give the title compound as a white, crystalline solid. PMR (CDCl$_3$): $\delta$1.39 (6H, s), 1.98 (2H, m), 3.08 (2H, m), 5.37 (2H, s), 7.20 (1H, d, J~8.3 Hz), 7.28 (2H, d, J~8.0 Hz), 7.34–7.48 (5H, m), 7.82 (1H, dd, J~8.3, 2.0 Hz), 8.14 (2H, d, J~8.0 Hz), 8.16 (1H, d, J~2.0 Hz).

Using this procedure, or the one described in Example 4, but substituting the appropriate precursors, the following compounds can be prepared:

butyl 4-((4,4-dimethyl-6-thiochromanoyl-ony) benzoate;
cyclohexyl 4-((4,4-dimethyl-6-thiochromanoyl-oxy)-benzoate;
ethyl 3-((4,4-dimethyl-6-thiochromanoyl-oxy)benzoate;
ethyl 2-((4,4-dimethyl-6-thiochromanoyl-oxy)benzoate;
ethyl 4-((2,2,4,4-tetramethyl-6-thiochromanoyl-oxy)-benzoate;
ethyl 3-((2,2,4,4-tetramethyl-6-thiochromanoyl-oxy)-benzoate; and
ethyl 2-((2,2,4,4-tetramethyl-6-thiochromanoyl-oxy)-benzoate.

EXAMPLE 6

4-((4,4-dimethyl-6-thiochromanoyloxy)benzoic acid

To a stirred solution of 580 mg (1.34) of benzyl 4-(4,4-dimethyl-6-thiochromanoyloxy)benzoate in 12 ml of methylene chloride at $-10°$ C. under nitrogen was added slowly 1.24 ml of a 1.0M (1.24 mmol) solution of boron tribromide in methylene chloride. The reaction mixture was stirred at $-10°$ C. for a further 2 h and then was quenched by the addition of ice. The organic layer was separated and the aqueous layer extracted with 2×25 ml methylene chloride. The organic extracts were combined and then washed with water and dried (MgSO$_4$). The solution was then filtered and the solvent removed in-vacuo. The resultant residue was purified by flash chromatography (silica; 20% ethyl acetate in hexane followed by 100% ethyl acetate) and then recrystallization from a mixture of ethyl acetate and ethanol to give the title compound as a white solid. PMR (CDCl$_3$): $\delta$1.39 (6H, s), 2.10 (2H, m), 3.10 (2H, m), 7.21 (1H, d, J~8.4 Hz), 7.28 (2H, d, J~8.7 Hz), 7.82 (1H, dd, J~8.4, 2.1 Hz), 8.14 (2H, d, J~8.7 Hz), 8.16 (1H, d, J~2.1 Hz).

Proceeding in the same or a similar manner, but substituting the appropriate ester prepared by Example 5, the following representative acids can be prepared:
3-((4,4-dimethyl-6-thiochromanoyloxy)-benzoic acid;
2-((4,4-dimethyl-6-thiochromanoyloxy)-benzoic acid;
4-((2,2,4,4-tetramethyl-6-thiochromanoyloxy)-benzoic acid; and
3-((2,2,4,4-tetramethyl-6-thiochromanoyloxy)-benzoic acid; and
2-((2,2,4,4-tetramethyl-6-thiochromanoyloxy)benzoic acid.

EXAMPLE 7

4-Hydroxyphenyl-3-methylbut-2-enylsulfide

A mixture of 2.11 g (52.7 mmol) of powdered sodium hydroxide and 7.38 g (52.7 mmol) of 4-hydroxythiophenol (90%) in 25 ml acetone was heated at reflux for 10 min. and then treated dropwise with a solution of 8.35 g (50.4 mmol) of 1-bromo-3-methyl-2-butene (90%) in 10 ml acetone over a period of 15 min. The mixture was heated at reflux for a further 1 hour, cooled to room temperature and the solvent then removed in-vacuo. The resultant residue was treated with water and extracted with 2×50 ml ether. The ether extracts were combined and washed successively with water and saturated NaCl solution and then dried (calcium chloride). The solution was filtered and concentrated in-vacuo and the resultant residue purified by flash chromatography (silica; 10% ethyl acetate in hexanes followed by 20% ethyl acetate in hexanes) to give the title compound as a pale yellow liquid. PMR (CDCl$_3$): $\delta$1.45 (3H, s), 1.68 (3H, s), 1.68 (3H, m), 3.42 (2H, d, J~7.9 Hz), 5.10 (1H, broad s), 5.26 (1H, t, J~7.9 Hz), 6.76 (2H, d, J~8.9 Hz), 7.29 (2H, d, J~8.9 Hz).

EXAMPLE 8

4-Acetoxyphenyl-3-methylbut-2-enylsulfide

A mixture of 6.87 g (35.4 mmol) of 4-hydroxyphenyl-3-methylbut-2-enylsulfide, 12.96 g (126 mmol) of acetic anhydride and 10 ml of pyridine was heated at reflux for 1.5 hours under a nitrogen atmosphere. The reaction mixture was cooled to room temperature, poured into water and extracted with 2×50 ml ether. The ether extracts were combined and washed successively with water and saturated NaCl solution and then dried (MgSO$_4$). The solution was filtered and the solvent removed in-vacuo to give the title compound as a pale yellow oil. PMR (CDCl$_3$): $\delta$1.55 (3H, s), 1.71 (3H, s), 2.29 (3H, s), 3.51 (2H, d, J~7.6 Hz), 5.28 (1H, m), 7.00 (2H, d, J~8.8 Hz), 7.35 (2H, d, J~8.8 Hz).

EXAMPLE 9

4,4-dimethyl-6-hydroxythiochroman

A mixture of 6.8 g (0.029 mmol) of 4-acetoxyphenyl-3-methylbut-2-enylsulfide and 17 g of 1:10 (w/w) phosphorus pentoxide in phosphoric acid was stirred at room temperature under nitrogen for 15 hours. The reaction mixture was then treated with water and stirred for 40 min. The mixture was then extracted with 2×50 ml ether. The ether extracts were combined and the solvent removed in-vacuo. The residue was then stirred under nitrogen with a solution of 1.93 g (0.034 mmol) of potassium hydroxide in 6 ml of water and 12 ml of ethanol for 1 hour. The ethanol was then removed from the mixture on the rotary evaporator and the aqueous solution then acidified to pHN2 with sulfuric acid. The acidified solution was extracted with 2×50 ml ether. The ether extracts were combined and washed successively with water and saturated NaCl solution and then dried (MgSO$_4$). The ether solution was then filtered and the solvent removed in-vacuo. The resultant crude product was purified by flash chromatography (silica; 20% ethyl acetate in hexanes) to give the title compound as a colorless, low-melting solid. PMR (CDCl$_3$): $\delta$1.25 (6H, s), 1.90 (2H, m), 2.97 (2H, m), 6.57

(1H, dd, J~8.6, 2.7 Hz), 6.88 (1H, d, J~2.7 Hz), 6.90 (1H, d, J~8.6 Hz).

EXAMPLE 10

Diethyl terephthallate

Hydrochloric acid gas was bubbled through 100 ml of absolute ethanol until the increase in weight of the ethanol was approximately 5 g. Then 16.6 g (0.1 mmol) of terepthallic acid was then added to the acidified ethanol and the mixture heated at reflux for 31 hours. The reaction mixture was cooled, then filtered and the residue washed with ethanol. The filtrate was concentrated in-vacuo and then poured into a mixture of water and 100 ml ether. After extraction, the ether layer was separated and washed successively with water and saturated sodium bicarbonate solution and then dried ($MgSO_4$). The ether solution was filtered and the solvent removed in-vacuo to give the title compound as a white solid. PMR ($CDCl_3$): δ1.42 (6H, t, J~7.0 Hz), 4.40 (4H, q, J~7.0 Hz), 8.10 (4H, s).

EXAMPLE 11

Ethyl hydrogenterephthalate

A soxlet extractor was charged with 3.83 g (0.022 mol) of anhydrous barium hydroxide and continuously extracted for 10 hours with hot ethanol into a refluxing mixture of 10 g (0.045 mmol) of diethyl terephthalate in 100 ml of absolute ethanol. The resultant white precipitate was filtered and then washed with ethanol. The precipitate was suspended in 100 ml ether and treated with excess dilute HCl. After extraction, the ether layer was separated and washed successively with water and saturated NaCl solution and then dried ($MgSO_4$). The ether solution was filtered and the solvent removed in-vacuo. The resultant residue was recrystallized from acetonitrile to give the title compound as a white solid. PMR ($CDCl_3$): δ1.40 (3H, t, J~7.0 Hz), 4.40 (2H, q, J~7.0 Hz), 8.10 (4H, s), 9.1 (1H, broad s).

EXAMPLE 12

Dibenzyl terephthalate

An amount equal to 48.5 g (0.25 mmol) of dimethyl terephthalate, 108 g (1.0 mmol) of benzyl alcohol and 0.5 g of potassium tert-butoxide were placed in a 500 ml, 3-necked round bottom flask fitted with a magnetic stir bar, a thermometer, a nitrogen inlet and an air condenser. The stirred mixture was heated at 140° C. for 15 hours while a rapid stream of nitrogen was passed over the surface of the mixture. Most of the excess benzyl alcohol was removed from the mixture by fractional distillation. The residue was dissolved in a mixture of ether and methylene chloride and silica was then added to the solution. The solution was then filtered and the solvent removed in-vacuo. The residual crude product was recrystallized from a mixture of hexanes and tert-butyl methyl ether to give the title compound as colorless crystals. PMR ($CDCl_3$): δ5.38 (4H, s), 7.35-7.50 (10H, m), 8.13 (4H, s).

EXAMPLE 13

Benzyl hydrogenterephthalate

To a heated mixture of 9.1 g (26 mmol) of dibenzyl terephthalate in 90 ml acetone and 30 ml water was added dropwise a solution of 1.05 g (25 mmol) of lithium hydroxide monohydrate in 10 ml of water and 10 ml of acetone. The reaction mixture was heated at reflux for a further 0.5 hours with vigorous stirring. The reaction mixture was allowed to cool and the aqueous solution was washed with 2×10 ml of ether. The aqueous layer was then acidified with glacial acetic acid and the resultant white precipitate extracted with 3×25 ml of ether. The ether extracts were combined and washed successively with water and saturated NaCl solution and then dried ($MgSO_4$). The ether solution was then filtered and the solvent removed in-vacuo. The resultant residue was recrystallized from a mixture of acetone and water to give the title compound as colorless crystals. PMR ($CDCl_3$): δ5.40 (2H, s), 7.36-7.49 (5H, m), 8.18 (4H, s).

EXAMPLE 14

Ethyl 4-(4,4-dimethyl-6-thiochromanoxyoyl)benzoate

A solution of 550 mg (2.8308 mmol) of 4,4-dimethyl-6-hydroxythiochroman, 556.1 mg (2.8637 mmol) of ethyl hydrogenterephthalate, 588.8 mg (2.8583 mmol) of 1,3-dicyclohexylcarbodiimide and 97.2 mg (0.7956 mmol) of 4-dimethylaminopyridine in 40 ml of methylene chloride was stirred at room temperature for 50 hours. The reaction mixture was then filtered and residue washed with 20 ml of methylene chloride. The filtrate was concentrated in-vacuo and the resultant crude product was purified by flash chromatography (silica 5% ethyl acetate in hexanes) to give the title compound as a white solid. PMR ($CDCl_3$): δ1.36 (6H, s), 1.45 (3H, t, J~7.0 Hz), 1.99 (2H, m), 3.06 (2H, m) 4.45 (2H, q, J~7.0 Hz), 6.95 (1H, dd, J~8.7, 2.4 Hz) 7.14 (1H, d, J~8.7 Hz), 7.22 (1H, d, J~2.4 Hz), 8.16 (2H, d, J~8.1 Hz), 8.26 (2H, d, J~8.1 Hz).

EXAMPLE 15

Benzyl 4,4-dimethyl-6-thiochromanyl terephthalate

A solution of 760 mg (3.9117 mmol) of 4,4-dimethyl-6-hydroxythiochroman, 1.0095 g (3.9394 mmol) of benzyl hydrogenterephthalate, 809.6 mg (3.9301 mmol) of 1,3-dicyclohexylcarbodiimide and 133.8 mg (1.0952 mmol) of 4-dimethylaminopyridine in 40 ml of methylene chloride was stirred at room temperature for 70 hours. The reaction mixture was then filtered and residue washed with 20 ml of methylene chloride. The filtrate was concentrated in-vacuo and the resultant crude product was purified by flash chromatography (silica, 6% ethyl acetate in hexanes) to give the title compound as a pale yellow oil. PMR ($CDCl_3$): δ1.33 (6H, s), 1.96 (2H, m), 3.03 (2H, m), 5.40 (2H, s), 6.92 (1H, dd, J~9.0, 2.4 Hz), 7.13 (1H, d, J~9.0 Hz), 7.20 (1H, d, J~2.4 Hz) 7.35-7.50 (5H, m), 8.19 (2H, d, J~8.1 Hz), 8.25 (2H, d, J~8.1 Hz).

Using the same or similar reagents and conditions, but substituting the appropriate starting materials, the following representative compounds can be made:
butyl 4,4-dimethyl-6-thiochromanyl beg-terephthalate;
cyclohexyl 4,4-dimethyl-6-thiochromanyl-terephthalate;
ethyl 4,4-dimethyl-6-thiochromanyl-isophthalate;
ethyl 4,4-dimethyl-6-thiochromanyl-phthalate;
ethyl 2,2,4,4-tetramethyl-6-thiochromanyl-terephthalate;
ethyl 2,2,4,4-tetramethyl-6-thiochromanyl-isophthalate; and
ethyl 2,2,4,4-tetramethyl-6-thiochromanyl-phthalate.

EXAMPLE 16

4,4-dimethyl-6-thiochromanyl hydrogen terephthalate

To a stirred solution of 480 mg (1.11 mmol) of benzyl (4,4-dimethyl-6-thiochromanyl)terephthalate in 8 ml of anhydrous methylene chloride at −78° C. was added under nitrogen 4.5 ml of 1M (4.5 mmol) boron tribromide in methylene chloride over 15 min. This reaction mixture was stirred at −78° C. for 1 hour and then poured into aqueous potassium acetate. The reaction mixture was acidified (pHN3) with dilute HCl and extracted with 3×10 of methylene chloride. The organic extracts were combined, washed with water and saturated NaCl and then dried (MgSO$_4$). The solution was filtered and the solvent removed in-vacuo. The residue was recrystallized from a mixture of acetone and hexanes to give the title compound as white crystals. PMR (CDCl$_3$): δ1.34 (6H, s), 1.97 (2H, m), 3.05 (2H, m), 6.94 (1H, dd, J∼8.1 Hz, 2.5 Hz), 7.14 (1H, d, J∼8.1 Hz), 7.25 (1H, d, J∼2.5 Hz), 8.25 (2H, A of AB, J∼8.1 Hz), 8.31 (2H, B of AB, J∼8.1 Hz).

This method, with appropriate substitution of starting materials, can be used to prepare the acids of this particular isomeric form, as illustrated by the following compounds:
4,4-dimethyl-6-thiochromanyl hydrogen isophthalate;
4,4-dimethyl-6-thiochromanyl hydrogen phthalate;
2,2,4,4-tetramethyl-6-thiochromanylhydrogenterephthalate;
2,2,4,4-tetramethyl-6-thiochromanylhydrogenisophthalate; and
2,2,4,4-tetramethyl-6-thiochromanylhydrogenphthalate.

EXAMPLE 17

3-bromophenyl-3-methylbut-2-enylsulfide

A mixture of 12.6 g (67 mmol) of 3-bromothiophenol and 4.1 g (102.5 mmol) of powdered NaOH in 50 ml of acetone was heated at reflux for 10 min. To the refluxing mixture was then added dropwise a solution of 10.9 g (73.2 mmol) of 1-bromo-3-methyl-2-butene in 20 ml of acetone. The reaction mixture was heated at reflux for 1 hour, cooled and the solvent removed in-vacuo. The residue was purified by flash chromatography (silica; 5% ethyl acetate in hexane) to give the captioned compound as a clear, yellow oil. PMR (CDCl$_3$): δ1.62 (3H, s), 1.73 (3H, s), 3.54 (2H, d, J∼8.1 Hz), 5.28 (1H, t, J∼8.1 Hz), 7.12 (1H, t, J∼7.8 Hz), 7.23 (1H, d, J∼7.8 Hz), 7.29 (1H, d, J∼7.8 Hz), 7.45 (1H, s).

EXAMPLE 18

4,4-Dimethyl-7-bromothiochroman and
4,4-dimethyl-5-bromothiochroman

To 45 ml of a 1:10 (w/w) mixture of phosphorus pentoxide and methanesulfonic acid was added slowly with stirring 7.0 g (27.24 mmol) of 3-bromophenyl-3-methylbut-2-enylsulfide. The mixture was stirred at room temperature for 15 minutes and then poured onto ice. The mixture was extracted with 2×30 ml ether. The ether extracts were combined and washed with water and saturated NaCl solution and then dried (MgSO$_4$). The solution was filtered and the solvent removed in-vacuo to give an approximately 85:15 mixture of the title isomers 4,4-dimethyl-7-bromothiochroman bromothiochroman and 4,4-dimethyl-5-bromothiochroman as a pale yellow oil. The mixture of isomers was used without further purification in the next step.

EXAMPLE 19

4,4-Dimethyl-7-carboxythiochroman

To a stirred solution of 1.0 g (3.9 mmol) of the 4,4-dimethyl-7-bromothiochroman and 4,4-dimethyl-5-bromothiochroman mixture in 12 ml of anhydrous ether at −78° C. was added, dropwise under nitrogen, 6.0 ml of 1.7M (10.2 mmol) tert-butyllithium in pentane. The reaction mixture was stirred at −78° C. for 1 hour and then a rapid stream of dry carbon dioxide gas was passed through it with vigorous stirring. The reaction mixture was warmed to −20° C. and then quenched with water. The mixture was warmed to room temperature and its pH adjusted to 10 with ammonium hydroxide. The basic solution was washed with 2×10 ml ether and then acidified with dilute HCl. The mixture was extracted with 3×20 ml of ether. The ether extracts were combined and washed with water and saturated NaCl solution and then dried (MgSO$_4$). The ether solution was filtered and the solvent removed in-vacuo. The residue was recrystallized from a mixture of ethyl acetate and hexane to give the captioned compound as a white solid. PMR (CDCl$_3$): δ1.33 (6H, s), 1.96 (2H, s), 3.04 (2H, m), 7.42 (1H, d, J∼8.1 Hz), 7.66 (1H, dd, J∼8.1 Hz, 1.8 Hz), 7.77 (1H, d, J∼1.8 Hz).

EXAMPLE 20

Ethyl 4-(4,4-dimethyl-7-thiochromanoyloxy)benzoate

A solution of 103.5 mg (0.466 mmol) of 4,4-dimethyl-7-carboxythiochroman and 77.8 mg (0.468 mmol) of ethyl 4-hydroxybenzoate in 10 ml of methylene chloride was treated sequentially with 14.2 mg (0.116 mmol) of 4-dimethylaminopyridine and 96.9 mg (0.47 mmol) of 1,3-dicyclohexylcarbodiimide. The reaction mixture was stirred at room temperature for 120 hours and then filtered and the residue washed with 10 ml of methylene chloride. The filtrate was concentrated in-vacuo and the residue purified by flash chromatography (silica; 5% ethyl acetate in hexanes) to give the title compound as a colorless oil. PMR (CDCl$_3$): δ1.38 (6H, s), 1.42 (3H, t, J∼7.1 Hz), 2.02 (2H, m), 3.08 (2H, m), 4.41 (2H, q, J∼7.1 Hz), 7.29 (2H, d, J∼8.7 Hz), 7.51 (1H, d, J∼8.3 Hz), 7.81 (1H, dd, J∼8.3 Hz, 1.9 Hz), 7.95 (1H, d, J∼1.9 Hz), 8.14 (2H, d, J∼8.7 Hz).

This same procedure can be used to make other compounds of this invention where A is C(O) and is at the 7-position on the thiochroman moiety.

EXAMPLE 21

5-(4-bromophenyl)-3,3-dimethylthioacrylate.

To an ice-bath cooled solution of 1.92 g (80 mmol) of NaH (obtained from a 60% suspension in mineral oil by 3×15 ml hexane wash) in 30 ml of dry tetrahydrofuran (THF) was added slowly under argon a solution of 15.1 g (80 mmol) of 4-bromothiophenol in 60 ml of dry THF over 1 h. The mixture was stirred at 0° C. for a further 30 minutes and then treated with a solution of 10.1 g (85 mmol) of dimethylacryloyl chloride in 30 ml of dry THF. The cooling bath was then removed and the mixture then stirred at room temperature for 40 h. The reaction mixture was poured into 200 ml of water containing 2 ml of glacial acetic acid and the organic layer was separated. The organic layer was washed with 2×75 ml of water and then dried (MgSO$_4$). The solvent was removed in-vacuo to give the title compound as a yellow oil.

PMR (CDCl$_3$): δ1.91 (3H, s), 2.14 (3H, s), 6.03–6.06 (1H, m), 7.28 (2H, d, J~8.6H$_z$), 7.53 (2H, d, J~8.6 Hz).

EXAMPLE 22

4,4-Dimethyl-6-bromo-2-oxothiochroman

To a stirred, ice-cooled suspension of 15.9 g (119 mmol) of aluminum chloride in 140 ml of methylene chloride was added under nitrogen a solution of 21.64 g (79.9 mmol) of 5-(4-bromophenyl)-3,3-dimethylthioacrylate in 100 ml of methylene chloride. The mixture was then stirred at room temperature for 2 h and then poured into 250 g of an ice and brine mixture. The mixture was extracted with methylene chloride and the combined organic extracts were washed with saturated NaCl solution and then dried (MgSO$_4$). The solvent was removed in-vacuo and the residue recrystallized from hexanes to give the title compound as white crystals. PMR (CDCl$_3$): δ1.40 (6H, s), 2.67 (2H, s), 7.31–7.40 (3H, m).

EXAMPLE 23

+-Bromo-2-(1,1,3-trimethyl-3-hydroxybutyl)thiophenol

To a solution of 3.0 g (11 minol) of 4,4-dimethyl-6-bromo-2-oxothiochroman in 30 ml of dry ether was added under nitrogen 37 ml of 3.0M (111 mmol) methyl magnesium chloride in THF. The reaction mixture was stirred at reflux temperature for 40 h and then at room temperature for 24 h. The reaction mixture was then poured onto a mixture of 100 g of ice and 8 ml of concentrated H$_2$SO$_4$. The mixture was extracted with ether, the ether extracts were combined and washed successively with saturated NaHCO$_3$; water and saturated NaCl and then dried (MgSO$_4$). The solvent was removed in-vacuo and the residue purified by flash chromatography (silica; 15% ethyl acetate in hexanes) to give the title compound as a pale yellow oil.

PMR (CDCl$_3$): δ1.05 (6H, s), 1.52 (6H, s), 2.30 (2H, s), 3.71 (1H, s), 7.22 (1H, dd, J~8.5 Hz, 2.1 Hz), 7.28 (1H, d, J~8.5 Hz), 7.35 (1H, d, J~2.1 Hz).

EXAMPLE 24

2,2,4,4-Tetramethyl-6-bromothiochroman.

A mixture of 500 mg (1.49 mmol) of 4-bromo-2-(1,1,3-trimethyl-3-hydroxybutyl thiophenol and 8 ml of 20% aqueous H$_2$SO$_4$ was heated at reflux for 24 h. The mixture was extracted with hexanes, the organic extracts were combined and washed successively with water, saturated NaHCO$_3$, water again, saturated NaCl and then dried (MgSO$_4$). The solvent was removed in-vacuo and the residue purified by flash chromatography (silica; hexanes) to give the title compound as a colorless oil. PMR (CDCl$_3$): δ1.35 (6H, s), 1.40 (6H, s), 1.93 (2H, s), 7.17 (1H, dd, J~8.4 Hz, 2.1 Hz) 7.23 (1H, d, J~8.4 Hz), 7.26 (1H, d, J~2.1 Hz).

EXAMPLE 25

2,2,4,4-Tetramethyl-6-carboxythiochroman

To a stirred solution of 240 mg (0.84 minol) of 2,2,4,4-tetramethyl-6-bromothiochroman in 1 ml of dry ether at −78° C. was added, dropwise under nitrogen, 1 ml of 1.7M (1.7 mmol) tert-butyl lithium in pentane. The reaction mixture was stirred at −78° C. for a further 2 h and then treated quickly with an excess of dry ice. The reaction mixture was warmed to room temperature and treated with 1 ml of water and 1 ml of ether. The aqueous layer was separated and the organic layer was extracted with 4×5 ml of water. The aqueous extracts were combined, acidified with HCl to a pH of 2 and then extracted with 2×15 ml of ether. The ether extracts were combined, washed with water and saturated NaCl solution and then dried (MgSO$_4$). The ether solution was filtered and the solvent removed in-vacuo to give the title compound as a white solid. PMR (CDCl$_3$): δ1.42 (6H, s), 1.43 (6H, s), 2.03 (2H, s), 7.50 (1H, d, J~8.4 Hz), 7.81 (1H, dd, J~8.4 Hz, 1.8 Hz), 7.89 (1H, d, J~1.8 Hz).

EXAMPLE 26

Ethyl 4-(2,2,4,4-tetramethyl-6-thiochromanoylozy)benzoate

A solution of 90 mg (0.36 mmol) of 2,2,4,4-tetramethyl-6-carboxythiochroman and 60 mg (0.36 mmol) of ethyl 4-hydroxybenzoate in 2 ml of methylene chloride was treated with a solution of 1,3-dicyclohexylcarbodiimide 74.4 mg (0.36 mmol) and 11 mg (0.09 mmol) of 4-dimethylaminopyridine in 1 ml of methylene chloride. The reaction mixture was stirred under nitrogen for 22 h and then filtered. The filtrate was concentrated in-vacuo and the residue purified by flash chromatography (silica, 10% ethyl acetate in hexane) to give the title compound as a colorless oil.

PMR (CDCl$_3$): δ1.43 (3H, t, J~7.2 Hz), 1.46 (6H, s), 1.47 (6H, s), 2.03 (2H, s), 4.42 (2H, q, J~7.2 Hz), 7.29 (2H, d, J~8.8 Hz), 7.54 (2H, d, J~8.3 Hz), 7.89 (1H, dd, J~8.3 Hz, 1.8 Hz), 7.99 (1H, d, J~1.8 Hz), 8.15 (2H, d, J~8.8 Hz)

EXAMPLE 27

2-Hydroxy-2,4,4-trimethyl-6-bromothiochroman

To 30 ml of 3.0M (90 mmol) of methyl magnesium chloride, cooled in an ice bath, was added under nitrogen a solution of 8 g (29.63 minol) of 4,4-dimethyl-6-bromo-2-oxotriochroman in 60 ml of dry ether over a period of 30 min. The cooling bath was then removed and the mixture stirred for 13 h. The reaction mixture was then poured onto a mixture of 200 g of ice and 6 ml of concentrated H$_2$SO$_4$. The organic layer was separated and the aqueous layer extracted with ether. The organic layers were combined and washed successively with water, saturated NaHCO$_3$ and saturated NaCl solutions and then dried (MgSO$_4$). The solvent was removed in vacuo and the residue purified by flash chromatography (silica; 9% ethyl acetate in hescane) to give the title compound as a white solid. PMR (CDCl$_3$): δ1.35 (3H, s), 1.47 (3H, s), 1.71 (3H, s), 2.02–2.17 (2H, m), 2.42 (1H, s), 7.17–7.28 (3H, m).

EXAMPLE 28

2,4,4-Trimethyl-6-bromo-2,3-dehydrothiochroman.

A mixture of 300 mg (0.99 minol) of 2-hydroxy-2,4,4-trimethyl-6-bromothiochroman and 4 ml of 20% aqueous H$_2$SO$_4$ was heated at reflux for 15 h. The mixture was then cooled, diluted with water and extracted with hexane. The organic extract was washed with water and saturated NaCl solution and then dried (MgSO$_4$). The ether solution was fitered and concentrated in vacuo to give the title compound as a pale yellow oil. PMR (CDCl$_3$): δ1.33 (6H, s), 1:99 (3H, d, J~1.4 Hz), 5.45 (1H, broad s), 7.19 (1H, d, J~8.4 H$_z$), 7.27 (1H, dd, J~8.4 Hz, 2.0 Hz), 7.30 (1H, d, J~2.0 Hz).

EXAMPLE 29

2,4,4-Trimethyl-6-bromothiochroman.

A solution of 2.69 g (10 minol) of 2,4,4-trimethyl-6-bromo-2,3-dehydrothiochroman in 100 ml of 1:1 ethanol/benzene was degassed under argon and then treated with 280 mg (0.3 minol) of tris(triphenylphosphine) rhodium (I) chloride. The mixture was shaken in a Parr Hydrogenation apparatus under 50 psi hydrogen pressure for 18 h. The solvent was removed in-vacuo and the residue was purified by flash chromatography (silica; hexane) to give the title compound.

EXAMPLE 30

(3-Methyl-4-bromo-phenyl)-3-methylbut-2-enyl sulfide

To a stirred solution of 9.52 g (68 mmol) of 3-methyl-4-bromothiophenol in 80 ml of acetone was added 2.86 g (68 mmol) of powdered sodium hydroxide and mixture stirred until dissolution was complete. The reaction mixture was then heated to reflux and then treated with a solution of 11.26 g (68 mmol) of 4-bromo-2-methyl-2-butene in 20 ml of acetone. The mixture was heated at reflux for a further 0.5 h, cooled to room temperature and the solvent removed in-vacuo. The residue was taken up in 35 ml of water and extracted with ether. The ether extracts were combined and washed successively with water and saturated NaCl solution and then dried ($MgSO_4$). The solvent was removed in-vacuo and the residue kugelrohr distilled (140°–145°, 0.2 mm) to give the title compound as a colorless oil. PMR ($CDCl_3$): $\delta 1.58$ (3H, s), 1.70 (3H, s), 2.33 (3H, s), 3.49 (2H, d, J~7.8 Hz), 5.26 (1H, t, J~7.8 Hz), 6.98 (1H, dd, J~8.3 Hz, 2.3 Hz), 7.17 (1H, d, J~2.3 Hz), 7.38 (1H, d, J~8.3 Hz)

EXAMPLE 31

4,4,7-Trimethyl-6-bromothiochroman

To 40 g of a vigorously stirred mixture of 10% phosphorus pentoxide in methanesulfonic acid was added slowly 6.0 g (28.8 mmol) of (3-methyl-4-bromophenyl)-3-methylbut-2-enyl-sulfide. The mixture was stirred at room temperature for a further 2 h and was then poured onto ice. The mixture was extracted with 2×40 ml of ether and the combined ether extracts were washed successively with water and saturated NaCl solution and then dried. The solvent was removed in-vacuo and the residue kugelrohr distilled (130° C.; 0.07 mm) to give the title compound as a viscous oil. PMR ($CDCl_3$): $\delta 1.28$ (6H, s) 1.84–1.93 (2H, m), 2.26 (3H, s), 2.95–3.03 (2H, m) 6.94 (1H, s), 7.46 (1H, s).

EXAMPLE 32

4,4,7-Trimethyl-6-Carboxythiochroman

A solution of 500 mg (1.85 mmol) of 4,4,7-trimethyl-6-bromothiochroman in 2.3 ml of dry ether was cooled to $-78°$ C. under nitrogen and then treated dropwise with 2.2 ml of 1.7M (3.74 mmol) tert-butyllithium in pentane. The reaction mixture was stirred at $-78°$ C. for a further 3 h and then a stream of dry carbon dioxide gas was bubbled through the mixture for 10 min. The mixture was allowed to warm to room temperature and then treated with 1 ml of ether and 5 ml of water. The aqueous layer was separated, acidified with dilute HCl and then extracted with 3×20 ml of ether. The ether extractions were combined and dried ($MgSO_4$). The ether solution was filtered and the solvent removed in-vacuo to give the title compound as a white solid. PMR ($CDCl_3$): $\delta 1.35$ (6H, s), 1.91–2.00 (2H, m), 2.55 (3H, s), 3.00–3.09 (2H, m), 6.99 (1H, s), 8.11 (1H, s).

EXAMPLE 33

Ethyl 4-(4,4,7-trimethyl-6-thiochromanoyloxy)benzoate

A solution of 83.7 mg (0.35 mmol) of 4,4,7-trimethyl-6-carboxythiochroman and 59.1 mg (0.35 mmol) of ethyl-4-hydroxybenzoate in 2 ml of methylene chloride was treated sequentially with 74.5 mg (0.36 mmol) of 1,3-dicyclohexylcarbodiimide and 11.1 mg (0.09 mmol) of 4-dimethylaminopyridine. The mixture was stirred under nitrogen for 24 h and then filtered. The fillrate was concentrated in-vacuo and the residue purified by flash chromatography (silica; 15% ethyl acetate in henane) to give the title compound as a pale yellow oil. PMR ($CDCl_3$): $\delta 1.37$ (6H, s), 1.41 (3H, t, J~7.1 Hz), 1.92–2.00 (2H, m), 2.56 (3H, s), 3.02–3.10 (2H, m), 4.40 (2H, q, J~7.1 Hz), 7.03 (1H, s), 7.29 (2H, d, J~8.7 Hz), 8.13 (2H, d, J~8.7 Hz), 8.18 (1H, s).

EXAMPLE 34

Preferably, these compounds may be administered topically using various formulations. Such formulation may be as follows.

| Ingredient | Weight/Percent |
| --- | --- |
| Solution | |
| Compound | 0.1 |
| BHT | 0.1 |
| Alcohol USP | 58.0 |
| Polyethylene Glycol 400 | 41.8 |
| Gel | |
| Compound | 0.1 |
| BHT | 0.1 |
| Alcohol USP | 97.8 |
| Hydroxypropyl Cellulose | 2.0 |

What is claimed is:
1. A Compound of the formula

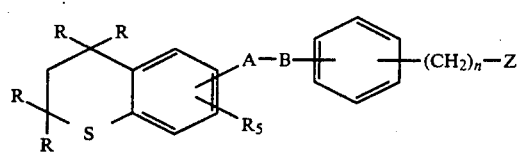

in which:
the R groups are independently hydrogen or lower alkyl;
$R_5$ is lower alkyl, $R_5$ being attached to the thiochroman ring at the 6 or at the 7-position;
one of A and B is O or S and the other is —C(O)—, being attached to the thiochroman ring at the unoccupied 6 or 7-position;
n is 0–5; and
Z is H, or Z is —COD where D is —OH, or OM wherein M is a pharmaceutically acceptable cation, or D is $OR_1$ where $R_1$ is a lower alkyl group, or D is —N($R_4$)$_2$ where
$R_4$ is hydrogen or a lower alkyl group, or Z is —OE where E is hydrogen or a $C_{1-20}$ aliphatic, cycloaliphatic, or aliphatic-phenyl ether-forming group, or a $C_{1-10}$ aliphatic or cycloaliphatic carboxylic acid ester forming group, or a phenyl or lower alkyl phenyl carboxylic acid ester forming group, or Z is —CHO or an acetal derivative thereof formed with a lower alkyl or cycloalkyl alcohol, or an acetal derivative thereof formed with an alkyl diol having 2 to 6 carbon atoms, or Z is —COR$_3$ where R$_3$ is —(CH$_2$)$_m$CH$_3$ where m is 0–4 and the sum of n and m does not exceed 4, or a ketal derivative thereof formed with a lower alkyl or cycloalkyl alcohol, or a ketal derivative thereof formed with an alkyl diol having 2 to 6 carbon atoms.

2. A compound of claim 1 where A is O and is attached to the thiochroman ring at the 6-position.

3. A compound of claim 2 where Z is COOH or said ester or said amide thereof, or said pharmaceutically acceptable salt thereof.

4. A compound of claim 1 where A is O and is attached to the thiochroman ring at the 7-position.

5. A compound of claim 4 where Z is COOH or said ester or said amide thereof, or said pharmaceutically acceptable salt thereof.

6. A compound of claim 1 where A is C=O and is attached to the thiochroman ring at the 6-position.

7. A compound of claim 6 where Z is COOH or said ester or said amide thereof, or said pharmaceutically acceptable salt thereof.

8. A compound of claim 7 which is ethyl 4-(4,4,7-trimethyl-6-thiochromanoyloxy)benzoate, 4-(4,4,7-trimethyl-6-thiochromanoyloxy)benzoic acid, or a pharmaceutically acceptable salt of the acid.

9. A compound of claim 7 which is ethyl 4-(2,2,4,4,7-pentamethyl-6-thiochromanoyloxy)benzoate, 4-(2,2,4,4,7-pentamethyl-6-thiochromanoyloxy)benzoic acid, or a pharmaceutically acceptable salt of the acid.

10. A compound of claim 1 where A is C=O and is attached to the thiochroman ring at the 7-position.

11. A compound of claim 10 where Z is COOH or said ester or said amide thereof, or said pharmaceutically acceptable salt thereof.

12. A compound of the formula

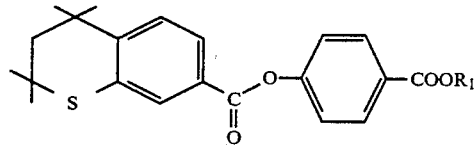

where R$_1$ is H or a lower alkyl group.

13. A compound of claim 12 where R$_1$ is hydrogen.

14. A compound of claim 12 where R$_1$ is ethyl.

15. A pharmaceutical composition comprising a pharmaceutically acceptable excipient and a compound of claim 1.

16. A method for treating psoriasis in a mammal which method comprises administering, alone or with a pharmaceutically acceptable excipient, a therapeutically effective amount of a compound of claim 1.

* * * * *

UNITED STATES PATENT AND TRADEMARK OFFICE
CERTIFICATE OF CORRECTION

PATENT NO. : 5,015,658
DATED : May 14, 1991
INVENTOR(S) : Roshantha A. S. Chandraratna It is certified that error appears in the above-identified patent and that said Letters Patent is hereby corrected as shown below:

Column 9, line 31, "goten" should be –gotten–;

Column 14, line 24, after "(3H, s)," (1st occur.) delete --1.68 (3H, s),--.

Signed and Sealed this

Twelfth Day of October, 1993

*Attest:*

BRUCE LEHMAN

*Attesting Officer*  *Commissioner of Patents and Trademarks*